(12) United States Patent
Santaniello et al.

(10) Patent No.: US 6,476,243 B1
(45) Date of Patent: Nov. 5, 2002

(54) PERFLUORINATED ESTERS OF ALKANOYL L-CARNITINE FOR THE PREPARATION OF CATIONIC LIPIDS FOR THE INTRACELLULAR DELIVERY OF PHARMACOLOGICALLY ACTIVE COMPOUNDS

(75) Inventors: Mosè Santaniello, Nettuno (IT); Lucia Critelli, Pomezia (IT); Nazareno Scafetta, Pavona di Albano (IT); Maria Grazia Cima, Civitavecchia (IT); Maria Ornella Tinti, Roma (IT); Claudio Pisano, Aprilia (IT); Andrea Pucci, Albano Laziale (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 41 days.

(21) Appl. No.: 09/670,620

(22) Filed: Sep. 27, 2000

Related U.S. Application Data

(63) Continuation of application No. PCT/IT99/00117, filed on May 4, 1999.

(30) Foreign Application Priority Data

May 6, 1998 (IT) .......................... RM98A0293

(51) Int. Cl.[7] .................................................. C07F 3/06
(52) U.S. Cl. ..................... 554/121; 554/123; 554/231; 554/225; 514/551; 560/170; 560/172
(58) Field of Search ............... 514/526, 527, 514/551; 560/155, 170, 185, 172; 554/121, 123, 225, 231

(56) References Cited

U.S. PATENT DOCUMENTS 4,439,438 A * 3/1984 Cavazza ...................... 424/263

FOREIGN PATENT DOCUMENTS

FR 2694195 * 4/1994 .......... A61K/37/48

OTHER PUBLICATIONS

Menotti Calvani et al, "L–Carnitine Esters as "Soft", Broad–Spectrum Antimicrobial Amphiphiles", J. Med. Chem., vol. 41 (1998), pp. 2227–2233.*
Bruce e. Smart et al, "Fluorinated Aliphatic Compounds", Kirk–Othmer Encyloc. Chem. Tech., (1994) vol. 11, pp. 499–521.*
Schail Malik et al, "Fast–atom–bombardment (FAB) mass spectrometry of new pentafluoropropyl esters of carnitine and its acy derivatives", Can. J. Appl. Spectrosc., vol. 37 (1992), pp. 142–144.*

* cited by examiner

Primary Examiner—Paul J. Killos
(74) Attorney, Agent, or Firm—Nixon & Vanderhye P.C.

(57) ABSTRACT

Perfluorinated esters of alkanoyl-L-carnitine of the formula (I):

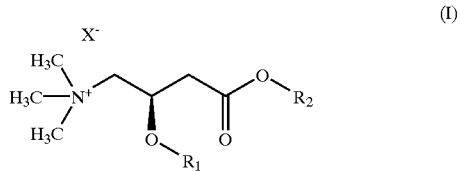

are useful as cationic lipids for the intracellular delivery of pharmacologically active compounds.

18 Claims, No Drawings

US 6,476,243 B1

PERFLUORINATED ESTERS OF ALKANOYL L-CARNITINE FOR THE PREPARATION OF CATIONIC LIPIDS FOR THE INTRACELLULAR DELIVERY OF PHARMACOLOGICALLY ACTIVE COMPOUNDS

This is a continuation of PCT application No. PCT/IT99/00117, filed May 4, 1999, the entire content of which is hereby incorporated by reference in this application.

The present invention relates to a class of perfluorinated esters of alkanoyl L-carnitine and their use as cationic lipids suitable for favouring the intracellular delivery of pharmacologically active compounds, facilitating their transmembrane transport, or for promoting their interaction with specific cell membrane sites (receptors).

What is meant by "intracellular delivery" is cellular transfection with polynucleotides endowed with therapeutic action and the introduction of antiviral drugs or immunogenic polypeptides into the cells.

Many of the pharmacologically active substances, such as, for instance, polypeptides and proteins or drugs in general need to penetrate into the cells to exert their effects by influencing cell functions at subcellular or molecular level. For these molecules the cell membrane constitutes a selectively impermeable barrier. The cell membrane, in fact, performs a protective function, preventing the entry of potentially toxic substances, but also that of compounds with therapeutic activity. The complex composition of the cell membrane includes phospholipids, glycolipids and proteins; its function is influenced by cytoplasmatic components such as $Ca^{++}$ and other ions, ATP, microfilaments, microtubules, enzymes and proteins that bind $Ca^{++}$. The interaction between the structural and cytoplasmatic components of the cells and the response to external signals are responsible for the selectivity shown by and the various different cell types. The barrier effect of the membranes can be overcome by combining substances in complexes with lipid formulations that reproduce the composition of naturally occurring membrane lipids. These lipids are capable of fusing with the membranes and of releasing the substances combined with them into the cells. The lipid complexes are capable not only of facilitating intracellular transfer by means of fusion with the membranes, but can also diminish the charge repulsion between the membrane and the molecule that has to penetrate into the cell. Amphipathic lipids, such as membrane phospholipids, form lipid vesicles or liposomes in the aqueous systems.

Liposomes are vesicles in which an aqueous volume is entirely enclosed by one or more membranes composed of lipid molecules, usually phospholipids. Phospholipids, which consist in a hydrophilic head and a pair of carbon chains (hydrophobic tail), are the main components of biological membranes. In aqueous solution the hydrophobic tails autoassociate to exclude water, while the hydrophilic heads interact with the medium, spontaneously forming populations of vesicles of varying diameters. The lipids are generally zwitterionic, neutral or anionic. These vesicles can be used as carriers of drugs, small molecules, proteins, nucleotides and plasmids.

Over recent years, the cationic liposomes, a class of positively charged vesicles prepared from synthetic lipids, have been extensively used for the transfer of genetic material into the cells. The negative charge of DNA can interact with the positive charges of the cationic lipids, forming a stable DNA-liposome complex. The simplicity and versatility of this technology have made liposomes an important vehicle for the delivery of genes for gene therapy in human subjects. Currently, most of the vectors used for gene therapy and approved by the NIH Recombinant Advisory Committee include viral and synthetic systems.

Viral infection involves a series of complex mechanism in order to be able to attack a specific cell and carry the DNA into the nucleus. The rationale for the use of viral vectors for gene therapy is based on the possibility of replacing the viral genes with genes that code for a therapeutic function, while eliminating the ability of the viral particle to infect the cells. The limitations of viral therapy have to do with those viral elements that may be immunogenic, cytopathic and recombinogenic.

Great hopes are placed in the use of cationic lipids for gene therapy. These vectors possess great potential compared with those of biological origin, since they are much safer, less toxic and are also capable of incorporating genes of large size. As compared with biological-type vectors, however, they have a low intracellular gene transcription yield. It should be borne in mind, however, that the use of such transfection system is in an initial stage of research. Cationic lipids play a very important role in the formation of the DNA-lipid complex, in cell-complex interaction, in fusion with the membrane, in DNA release inside the cell and in transcription.

There are important examples of in-vivo applications of cationic liposomes. The first clinical trial on gene therapy was conducted by introducing an expression vector containing the human liposome-complexed HLA-B7 gene for the treatment of melanoma. Another important application relates to the treatment of pulmonary cystic fibrosis by means of the administration via the pulmonary route or as a nasal spray of the liposome-complexed expression vector SV-40C-FTR. Other clinical trials involving the use of liposomes in gene therapy for cancer are currently in progress.

Four constituent elements are generally identified in the structure of cationic lipids: the positively charged cationic head, the spacer, the anchor lipid and the linker bond.

The cationic head is responsible for the interactions between cationic liposomes and DNA, between the DNA-liposome complex and the cell membrane and the other components of the cell. It consists of mono- or polycationic groups (depending on the number of charges) that can be variably substituted.

The spacer is part of the molecule that separates the cationic head from the hydrophobic tail and is involved in ensuring optimal contact between the cationic head and the negative charges of the DNA phosphates.

The anchor lipid is the non-polar hydrocarbon part of the molecule and determines the physical properties of the double lipid layer, such as its rigidity and rate of exchange with membrane lipids.

What is meant by "linker bond" is the bond between the hydrocarbon chains and the rest of the molecule. This bond determines the chemical stability and biodegradability of the cationic lipids.

The scientific and patent literature is rich in references to the preparation and use of liposomes: however, only patent application EP 0 279 887 A2 describes the use of a derivative of carnitine, i.e. phosphatidyl carnitine, optionally in mixtures with other phospholipids and lipids (cholesterol, phosphatidyl choline, phosphatidyl serine), for the preparation of liposomes.

In the only example provided regarding the preparation of liposomes, liposomes of phosphatidyl carnitine are produced which incorporate propranolol, and drug known to be active as an antihypertensive, anti-angina and antiarrhythmia agent. The carnitine derivative is used here on account of the pronounced myocardial tropism of carnitine. This tropism makes it possible to avoid the liposomes being metabolised by the liver, rather than reaching the desired target site.

The presence of phosphatidyl carnitine also makes it possible to administer the liposomes orally, since they are resistant to intestinal lipases.

It has now been found that cationic lipids with a potent action favouring intracellular delivery of biologically active compounds consist in the perfluorinated ester of alkanoyl L-carnitine with the following formula (I):

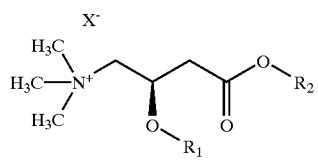

(I)

where:

R$_1$ is alkanoyl, linear or branched, with 2–20, and preferably 4–12 carbon atoms, optionally perfluorinated R$_2$ is perfluorinated alkyl, linear or branched, with 4–20, and preferably 5–12, carbon atoms; and X is the anion of a pharmacologically acceptable acid.

Therefore, it is an object of the present invention cationic liposomes consisting of perfluorinated esters of L-carnitine of formula (I). Esters of formula (I) are new, accordingly, they represent a further object of the present invention, together with their use in the preparation of cationic liposomes.

Another object of the present invention is the use of a cationic liposome as above defined for the preparation of a medicament useful for the intracellular delivery of a pharmacologically active compound, said medicament being also useful for promoting the interaction of a pharmacologically active compound with cell membrane receptors. In particular, according to the present invention, the pharmacologically active compound is a gene, optionally comprised in a suitable vector. Therefore, the medicament provided by the present invention is useful for gene therapy, for example wherein said gene is β-gal.

Examples of R$_1$, though not exclusively these are: acetyl, propionyl, butyryl, valeryl, isovaleryl, undecanoyl, lauroyl, tridecafluoroheptanoyl, heptadecafluorononanoyl, heptacosafluoromyristoyl, pentadecafluoro-octanoyl and 5H-octafluoropentanoyl.

What is meant here by "perfluorinated" R$_2$ is an alkyl in which at least 40% of the hydrogen atoms are replaced by fluorine atoms. Examples of such alkyls, though not exclusively these, are:

1,1H-2,2H-tridecafluoro-octyl;
1,1H-2,2H-3,3H-pentafluoropentyl;
1,1H-2,2H-nonafluorohexyl;
1,1H-2,2H-3,3H-4,4H-5,5H-6,6H- nonafluorodecyl;
1,1H-2,2H-heptadecafluorodecyl;
1,1H-2,2H-heinicosafluorododecyl; and
1,1H-tricosafluorododecyl.

What is meant by pharmacologically acceptable acid is the anion of an acid that does not give rise to unwanted toxic or side effects.

These acids are well known to pharmacologists and experts in pharmaceutical technology.

Examples of these anions, though not exclusively the ones listed, are: chloride: bromide; iodide; aspartate; acid aspartate; citrate; acid citrate; tartrate; mucate; phosphate; acid phosphate; fumarate; acid fumarate; glycerophosphate; glucose phosphate; lactate; maleate; acid maleate; orotate; oxalate; acid oxalate; sulphate; acid sulphate; trichloroacetate; trifluoroacetate and methane sulphonate.

Here below are provided a number of non-exclusive examples of the preparation of compounds according to the invention described herein.

EXAMPLE 1

Preparation of undecanoyl-L-carnitine chloride 1, 1H-2,2H-hepatdecafluorodecyl ester (ST 1223)

Undecanoyl-L-carnitine chloride (6.6 g; 0.018 mol), previously vacuum-dried at 40 ° C., was dissolved in 20 mL of anhydrous CH$_2$Cl$_2$. Thionyl chloride (2.2 mL; 0.03 mol) was added dropwise to the solution thus obtained at 0 ° C. under stirring.

The resulting mixture, the temperature of which was brought up to room temperature, was kept under stirring for 3 h. Later, the solution was vacuum-concentrated, the residue recovered with CH$_2$Cl$_2$ (50 mL 3 times) and the solution again vacuum-concentrated.

The undecanoyl-L-carnitine acid chloride thus obtained was solubilised in 20 mL of anhydrous methylene chloride and the resulting solution added dropwise at 0° C. to 1,1H-2,2H-hepatdecafluorodecanol-1 (13.9 g; 0.03 mol).

The resulting mixture was kept for one night under stirring at room temperature.

Later, petroleum ether was added up to complete precipitation of an oily product.

The crude reaction produce was purified by silicon gel chromatography, eluting with CHCl$_3$; CHCl—MeOH 95.5. 4 g of titre product were obtained. Yield 27%.

Elemental analysis for $C_{28}H_{39}NO_4F_{17}Cl$:

|  | C % | H % | N % | Cl % | F % |
|---|---|---|---|---|---|
| Calculated | 41.4 | 4.84 | 1.72 | 4.36 | 39.77 |
| Found | 40.03 | 4.77 | 0.86 | 5.68 | 38.9 |

$[\alpha]_D^{25} = -8.98$ (C = 1% MeOH)

HPLC

Column: μBondapak - C18 (10 μm) 3.9 mm×300 mm

Temp. 30° C.

Eluent CH$_3$CN/NH$_4$H$_2$PO$_4$ 50 mM 80/20 pH=3.0

Flow rate 1.0 mL/min

Rt 19.42 min

NWR CDCl$_3$δ 5.7(1H,m,C̲HOCO); 4.5–4.4(3H,d+t,N$^+$—C̲HH+COOCH$_2$);

4.0(1H,m,N$^+$CHH̲); 3.5(9H,s,(CH$_3$)$_3$$^+$N); 3.0–2.8(2H,m, CH$_2$COO);

2.5(2H,m,CH$_2$—CF$_2$); 2.3(2H,t,OCOCH$_2$); 1.5(2H,m, OCOCH$_2$C̲H$_2$);

1.2(14H,s,(CH$_2$($_7$); 0.9(3H,t, CH$_3$).

EXAMPLES 2–6

The following compounds:

Lauroyl-L-carnitine chloride 1,1H-2,2H-tridecafluoro-octyl ester (ST 1221);

Lauroyl-L-carnitine chloride 1,1H-2,2H-3,3H-pentafluoropentyl ester (ST 1245);

Undecanoyl-L-carnitine chloride 1,1H-2,2H-nonafluorohexyl ester (ST 1246);

Isovaleryl-L-carnitine chloride 1,1H-2,2H-3,3H-4,4H-5,5H-6,6H-nonafluorodecyl ester (ST 1192); and Undecanoyl-L-carnitine chloride (1,1H-2,2H-3,3H-4,4H-5,5H-6,6H-nonafluorodecyl ester (ST1193);

were prepared as described in example 1.

The following table gives a number of significant physico-chemical data for these compounds.

β-galactosidase) were diluted sterilely in 50 μl of HBS (HEPES 20 mM; NaCl 150 mM, pH 7.4)

Solution B: the liposome, prepared according to EXAMPLE 7, was diluted in distilled $H_2O$ to a concentration of 1.29 mM and 15 μL of this solution were diluted in 50 82 L of distilled $H_2O$).

The two solutions were mixed by stirring gently and incubated for 10–30 min at room temperature.

This procedure makes it possible to complex the DNA that has a net negative charge with the positively charged liposomes, thus forming the liposome-DNA complex.

| ST EXAMPLE | $R_1$ | $R_2$ | [α] | NMR δ $CDCl_3$ | HPLC |
|---|---|---|---|---|---|
| 1221 Ex. 2 | Lauroyl | 1.1H–2.2H | −5.5 (c = 1% $CHCl_3$) | 5.7(1H, m, CHOCO); 4.5–4.3(3H, m, $N^+C\underline{H}H$+$COOCH_2$); 4.0(1H, m, $N^+CH$ H); 3.4(9H, s, $(CH_3)_3N^+$); 3.0–2.8(2H, m, $CH_2COO$); 2.5(2H, m, $CH_2$—$CF_2$); 2.3(2H, t, $OCOCH_2$); 1.6(2H, m, $CH_2$); 1.2(16H, s, $(CH_2)_8$); 0.8(3H, t, $CH_3$) | *Rt 33.2 min |
| 1245 Ex. 3 | Lauroyl | 1.1H–2.2H–3.3H | −13.7 (c = 1% MetOH) | 5.7(1H, m, CHOCO); 4.5(1H, d, $N^+\underline{CH}$ H); 4.2(2H, t, $COOCH_2$); 4.0(1H, m, $N^+CH$ H); 3.5(9H, s, $(CH_3)_3N^+$); 3.0–2.8(2H, m, $CH_2COO$); 2.4(2H, t, $OCOCH_2$); 2.2–1.9(4H, m, $CH_2CH_2CF_2$), 1.6(2H, m, $CH_2$); 1.3(16H, s, $(CH_2)_8$); 0.9(3H, t, $CH_3$). | **Rt 5.28 min |
| 1246 Ex. 4 | Undecanoyl | 1.1H–2.2H | −13.4 (c = 1% $H_2O$) | 5.7(1H, m, CHOCO); 4.5(1H, d, $N^+CH$ $\underline{H}$); 4.4(2H, t, $COOCH_2$); 4.0(1H, m, $N^+$ CH $\underline{H}$); 3.5(9H, s, $(CH_3)_3N^+$); 3.0–2.8(2H, m, $CH_2COO$), 2.4–2.6(2H, m, $CH_2CF_2$); 2.3(2H, t, $OCOCH_2$); 1.4(2H, m, $CH_2$); 1.2(14H, s, $(CH_2)_7$); 0.8(3H, t, $CH_3$) | **Rt 5.05 min |
| 1192 Ex. 5 | Isovaleryl | 1.1H–2.2H–3.3H–4.4H–5.5H–6.6H | −12 (c = 1% MetOH) | 5.7(1H, m, CHOCO); 4.3(1H, d, $N^+CH$ $\underline{H}$); 4.1(3H, m, $N^+$ —$C\underline{H}$ H+$COOCH_2$); 3.5(9H, s, $(CH_3)_3N^+$); 2.9–2.8(4H, $CH_2COO$+$OCOCH_2$); 2.2(2H, m, $CH_2CF_2$); 2.1(1H, m, $C\underline{H}(CH_3)_2$); 1.7(4H, m, $(CH_2)_2$); 1.4(4H, m, $(CH_2)_2$); 0.9(6H, d, $CH(C\underline{H}_3)_2$). | ***Rt 9.30 min |
| 1193 Ex. 6 | Undecanoyl | 1.1H–2.2H–3.3H–4.4H–5.5H–6.6H | −10.7 (c = 1% MetOH) | 5.6(1H, m, CHOCO); 4.3(1H, d, $N^+CH$ $\underline{H}$); 4.1(3H, m, $N^+$ $C\underline{H}H$+$OCH_2$); 3.5(9H, s, $(CH_3)_3N^+$); 2.8(2H, m, $CH_2COO$); 2.3(4H, 2t, $OCOCH_2CH_2CF_2$); 2.0(2H, m, $CH_2$); 1.6(2H, m, $(CH_2)_3$); 1.4(2H, m, $CH_2$); 1.2(14H, m, $(CH_2)_7$); 0.9(3H, t, $CH_3$). | *Rt 15 min |

*as in example 1, eluent $CH_3CH/NH_4H_2PO_4$ 70/30
**Column  SCX-SGE (5 μm); 4.0 mm × 250 mm
Temp.  30° C.
Eluent  $CH_3CH/NH_4H_2PO_4$ 25 mM 60/40 pH = 4
Flow rate  0.75 mL/min
***as in example 1, eluent $CH_3CH/NH_4H_2PO_4$ 50 mM 60/40

EXAMPLE 7

Preparation of ST1223 liposomes used in transfection assays

Liposomes were prepared starting with 200 mg of ST1223, synthesised according to the procedure described in EXAMPLE 1 and solubilised in 50 mL of chloroform (solubilisation phase). The solvent was then eliminated under vacuum for one night (t 30–40° C.; 400–700 mm Hg). The sample was hydrated with deionised water to a final concentration of 5 mM (hydration phase). The liposomes were then subjected to sonication for 1 h at 10-second intervals using a sonication bath. The liposomes thus prepared produced unilaminar vesicles.

EXAMPLE 8

Formation of ST1223 -DNA liposome complex

The liposome-DNA complex was prepared by mixing the two solutions A and B described here below:
Solution A: 2.5 μg of plasmid DNA (pCMV/β- Gal, 7200 base pairs, used for the expression of the enzyme

EXAMPLE 9

Transfection Protocol

The efficiency of transfection mediated by cationic liposomes is influenced by various parameters such as the presence or absence of serum in the incubation medium, and the cell line and density. DNA transfection was performed according to the following parameters:

Presence of serum

It is known in the literature that the presence of serum in the incubation medium may inhibit transfection mediated by cationic liposomes. Our experiments were carried out in the presence of serum (fetal calf serum) and, even so, demonstrated activity.

Choice of cell lines pCMV-β-Gal plasmid DNA transfection was done on 4 different cell lines:

HeLa human uterine carcinoma

MCF-7 human mammary adenocarcinoma

Caco2 human colon adenocarcinoma

T98-G human glioblastoma

Cell density pCMV-β-Gal DNA transfection mediated by cationic liposomes in the various cell lines HeLa, MCF-7, Caco2, and T98-G was performed at different cell densities: 100,000 cells/dish 200.000 cells/dish and 300.000 cells/dish. The greatest transfection efficiency was observed at a density of 100.000 cells/dish for Caco2, 200.000 cells/dish for HeLa and MCF-7, and 300.000 cells/dish for T98-G.

The transfection procedure is described as follows:

HeLa, MCF-7, Caco2 and T98-G cells were grown for 48 h (37° C., 5% $CO_2$) in the following growth media:
HeLa cells RPMI-1640 (HyQ catalogue), 10% fetal calf serum, 1% L-glutamine, 1% streptomycin, 1% penicillin
MCF-7 cells DMEM (Dulbecco Modified Eagle Medium, SIGMA catalogue), 10% fetal calf serum, 1% L-glutamine, 1% streptomycin, 1% penicillin
Caco2 cells EMEM (Essential Minimum Eagle Medium, SIGMA catalogue), 15% fetal calf serum, 1% L-glutamine, 1% streptomycin, 1%, penicillin
T98-G cells EMEM (Essential Minimum Eagle Medium, SIGMA catalogue), 10% fetal calf serum, 1% L-glutamine, 1% streptomycin, 1% penicillin.

Cells were plated at different densities (100.000 cells/dish, 200.000 cells/dish, 300.000 cells/dish) in Petri dishes (Corning or Falcon) measuring approximately 3 cm in diameter and incubated in 2 mL of medium for 18 h before being treated.

After replacing the medium with 2 mL of fresh medium, 100 μm of the liposome-DNA complex, prepared as described in EXAMPLE 8, were added to each dish; after gentle stirring, the dishes were placed in a thermostat for 5 h (37° C., 5% $CO_2$). Later, the cells were washed three times with 5 mL PBS buffer (Gibco catalogue) per dish and incubated for 16 h (37° C., 5% $CO_2$).

After washing the cells three times with 5 mL PBS buffer (Gibco catalogue) per dish, total proteins were extracted and 50 μg of these were loaded per well in order to determine β-galactosidase production by immunoassay (β-Gal ELISA Kit, Boehringer).

EXAMPLE 10

Table 1 and FIG. 1 give the expression data for the enzyme β-galactosidase (β-Gal) as a function of cell density in HeLa cells. The transfection procedure is described in EXAMPLE 9.

TABLE 1

| Density (cells/dish) | Total proteins (μg/dish) | β-Gal (pg/dish) |
|---|---|---|
| 100.000 | 141 | 87 |
| 200.000 | 282 | 303 |
| 300.000 | 413 | 83 |

Table 2 and FIG. 1 give the expression data for the enzyme β-galactosidase (β-Gal) as a function of cell density in MCF-7 cells. The transfection procedure is described in EXAMPLE 9.

TABLE 2

| Density (cells/dish) | Total proteins (μg/dish) | β-Gal (pg/dish) |
|---|---|---|
| 100.000 | 99 | 234 |
| 200.000 | 205 | 422 |
| 300.000 | 276 | 409 |

Table 3 and FIG. 1 give the expression data for the enzyme β-galactosidase (β-Gal) as a function of cell density in T98-G cells. The transfection procedure is described in EXAMPLE 9.

TABLE 3

| Density (cells/dish) | Total proteins (μg/dish) | β-Gal (pg/dish) |
|---|---|---|
| 100.000 | 75 | 126 |
| 200.000 | 129 | 330 |
| 300.000 | 218 | 491 |

Table 4 and FIG. 1 give the expression data for the enzyme β-galactosidase (β-Gal) as a function of cell density in Caco2 cells. The transfection procedure is described in EXAMPLE 9.

TABLE 4

| Density (cells/dish) | Total proteins (μg/dish) | β-Gal (pg/dish) |
|---|---|---|
| 100.000 | 42 | 422 |
| 200.000 | 132 | 395 |
| 300.000 | 193 | 385 |

What is claimed is:

1. A perfluorinated ester of alkanoyl-L-carnitine of the formula (I):

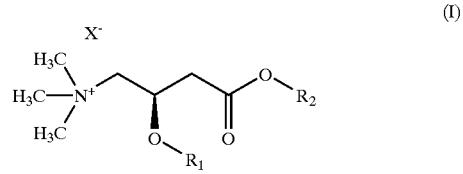

where:
   $R_1$ is alkanoyl, linear or branched, with 2–20 carbon atoms optionally perfluorinated, in which at least 40% of the hydrogen atoms are replaced by fluorine atoms or polyfluorinated;
   $R_2$ is perfluorinated alkyl, linear or branched, with 4–20 carbon atoms; and
   X is the anion of a pharmacologically acceptable acid.

2. An ester according to claim 1 in which $R_1$ is selected from the group consisting of acetyl, propionyl, butyryl, valeryl, isovaleryl, undecanoyl, lauroyl, tridecafluoroheptanoyl, heptadecafluorononanoyl, heptacosafluoromyristoyl, pentadecafluoro-octanoyl and 5H-octafluoropentanoyl.

3. An ester according to claim 1 or 2 in which $R_2$ is selected from the group consisting of 1,1H-2,2H-tridecafluoro-octyl; 1,1H-,2,2H-3,3H-pentafluoropentyl; 1,1H2,2H-nonafluorohexyl; 1,1H-2,2H-3,3H-4,4H-5,5H-6,6H-nonafluorodecyl; 1,1H-2,2H-heptadecafluorodecyl;

1,1H-2,2H-heinicosafluorododecyl; and 1,1H-tricosafluorododecyl.

4. An ester according to claim 1, in which $R_1$ has 4–12 carbon atoms and $R_2$ has 5–12 carbon atoms.

5. An ester according to claim 1 or 2 in which X is selected from the group consisting of chloride; bromide; iodide; aspartate; acid aspartate; citrate; acid citrate; tartrate; mucate; phosphate; acid phosphate; fumarate; acid fumarate; glycerophosphate; glucose phosphate; lactate; maleate; acid maleate; orotate; oxalate; acid oxalate; sulphate; acid sulphate; trichloroacetate; trifluoroacetate and methane sulphonate.

6. A liposome containing a perfluorinated ester of alkanoyl carnitine with formula (I):

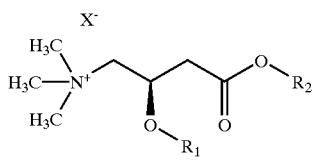

(I)

where $R_1$ is alkanoyl, linear or branched, with 2–20 carbon atoms, optionally perfluorinated in which at least 40% of the hydrogen atoms are replaced by fluorine atoms;

$R_2$ is polyfluorinated alkyl, linear or branched, with 4–20 carbon atoms; and

X is the anion of a pharmacologically acceptable acid.

7. A liposome according to claim 6 in which $R_1$ is selected from the group consisting of acetyl, propionyl, butyryl, valeryl, isovaleryl, undecanoyl, lauroyl, tridecafluoroheptanoyl, heptadecafluorononanoyl, heptacosafluoromyristoyl, pentadecafluorooctanoyl and 5H-octafluoropentanoyl, $R_2$ is selected from the group consisting of 1,1H-2,2H-tridecafluoro-octyl; 1,1H-2,2H-3,3H-pentafluoropentyl; 1,1H-2,2H-nonafluorohexyl; 1,1H-2,2H-3,3H-4,4H-5,5H-6,6H-nonafluorodecyl; 1,1H-2,2H-heptadecafluorodecyl; 1,1H-2,2H-heinicosafluorododecyl; and 1,1H-tricosa.fluorododecyl, and X is selected from the group consisting of chloride; bromide; iodide; aspartate; acid aspartate; citrate; acid citrate; tartrate; mucate; phosphate; acid phosphate; fumarate; acid fumarate; glycerophosphate; glucose phosphate; lactate; maleate; acid maleate; orotate; oxalate; acid oxalate; sulphate; acid sulphate; trichloroacetate; trifluoroacetate and methane sulphonate.

8. A method for the intracellular delivery of a pharmacologically active compound comprising administering a cationic liposome of claim 6.

9. The method of claim 6, in which the liposome promotes interaction of a pharmacologically active compound with cell membrane receptors.

10. The method according to claim 8, wherein said pharmacologically active compound is a gene, optionally resident in a vector.

11. A method for the intracellular delivery of a gene comprising administering a cationic liposome of claim 6 containing a gene.

12. The method according to claim 10 or 11, wherein said gene is β-gal.

13. Undecanoyl-L-carnitine chloride 1,1H-2,2H-heptadecafluorodecyl ester.

14. Lauroyl-L-carnitine chloride, 1,1H-2,2H-tridecafluoro-octyl ester.

15. Lauroyl-L-carnitine chloride 1,1H-2,2H-3,3H-pentafluoropentyl ester.

16. Undecanoyl-L-chloride 1,1H-2,2H-nonafluorohexyl ester.

17. Isovaleryl-L-carnitine chloride 1,1H-2,2H-3,3H-4,4H-5,5H-6,6H nonafluoro-decyl ester.

18. Undecanoyl-L-carnitine chloride 1,1H-2,2H-3,3H-4,4H-5,5H-6,6H nonafluoro-decyl ester.

* * * * *